(12) United States Patent
Dai et al.

(10) Patent No.: US 11,110,302 B2
(45) Date of Patent: Sep. 7, 2021

(54) MULTI-ROBOTIC ARM APPARATUS FOR INTRAOPERATIVE RADIOTHERAPY

(71) Applicant: Cancer Hospital, Chinese Academy of Medical Sciences, Beijing (CN)

(72) Inventors: Jianrong Dai, Beijing (CN); Chuanmeng Niu, Beijing (CN); Pan Ma, Beijing (CN); Minghui Li, Beijing (CN)

(73) Assignee: Cancer Hospital, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 15/978,545

(22) Filed: May 14, 2018

(65) Prior Publication Data

US 2021/0001154 A1 Jan. 7, 2021

(30) Foreign Application Priority Data

May 15, 2017 (CN) .......................... 201710338703.9

(51) Int. Cl.
*A61N 5/10* (2006.01)
(52) U.S. Cl.
CPC .... *A61N 5/1083* (2013.01); *A61N 2005/1058* (2013.01)
(58) Field of Classification Search
CPC .......... A61N 5/1083; A61N 5/10–1084; A61N 2005/1085–1098
See application file for complete search history.

(56) References Cited

U.S. PATENT DOCUMENTS

| 5,321,271 A | 6/1994 | Schonberg | |
|---|---|---|---|
| 5,635,721 A | 6/1997 | Bardi | |
| 2004/0068169 A1* | 4/2004 | Mansfield | A61B 6/4452 600/407 |
| 2009/0003975 A1* | 1/2009 | Kuduvalli | A61N 5/1049 414/146 |
| 2009/0296886 A1* | 12/2009 | Maltz | A61B 6/4458 378/65 |
| 2010/0069920 A1* | 3/2010 | Naylor | A61B 34/71 606/130 |

(Continued)

FOREIGN PATENT DOCUMENTS

| CN | 1537657 A | 10/2004 |
|---|---|---|
| CN | 204582331 U | 8/2015 |

(Continued)

OTHER PUBLICATIONS

Search Report by the National Intellectual Property Administration, PRC (China Patent Office) dated Feb. 27, 2019.

(Continued)

*Primary Examiner* — Thaddeus B Cox
(74) *Attorney, Agent, or Firm* — Radlo & Su

(57) ABSTRACT

A multi-robotic arm apparatus for intraoperative radiotherapy is provided. The apparatus may comprise a chassis, a main robotic arm mounted on the chassis for moving a radiation head installed at an end thereof, a first robotic arm mounted on the chassis having a first robotic arm end gripper for gripping an imaging device or a treatment applicator; and a second robotic arm mounted on the chassis having a second robotic arm end gripper for gripping a simulation applicator.

14 Claims, 4 Drawing Sheets

(56) References Cited

U.S. PATENT DOCUMENTS

| | | | | |
|---|---|---|---|---|
| 2012/0035470 A1* | 2/2012 | Kuduvalli | ................ | A61N 5/10 600/427 |
| 2013/0066135 A1* | 3/2013 | Rosa | ........................ | A61N 5/10 600/1 |
| 2013/0336449 A1* | 12/2013 | Tanabe | ................. | A61N 5/1067 378/62 |
| 2015/0283406 A1* | 10/2015 | Chang | .................. | A61B 6/4429 378/65 |
| 2016/0183899 A1* | 6/2016 | Vancamberg | ........ | A61B 6/4476 378/37 |
| 2016/0220844 A1* | 8/2016 | Paysan | ................... | G16H 10/60 |
| 2018/0085175 A1* | 3/2018 | Steinle | .................. | G06T 7/0012 |

FOREIGN PATENT DOCUMENTS

| | | |
|---|---|---|
| CN | 1050799CN1086 A | 11/2015 |
| CN | 105879244 A | 8/2016 |
| DE | 10331780 | 3/2005 |
| WO | WO 2012163983 | 6/2012 |

OTHER PUBLICATIONS

English Abstract of Chinese Published Patent Application CN204582331U.

English Abstract of Chinese Published Patent Application CN105879244A.

English Abstract of Chinese Published Patent Application CN105079986A.

English Abstract of Chinese Published Patent Application CN1537657A.

* cited by examiner

MULTI-ROBOTIC ARM APPARATUS FOR INTRAOPERATIVE RADIOTHERAPY

CROSS REFERENCE TO RELATED APPLICATIONS

This application is a continuation application of Chinese Application No. CN 201710338703.9, filed on 15 May 2017, the entire disclosure of which is incorporated by reference herein in its entirety.

TECHNICAL FIELD

The present invention generally relates to the field of medical radiotherapy, and more particularly, to an apparatus for intraoperative radiotherapy with multiple robotic arms.

BACKGROUND

Intraoperative radiotherapy (IORT) is one of the technologies for radiotherapy in tumor treatment, which applies, in a surgical field of vision, therapeutic levels of high-energy electron beam radiation to a tumor bed, a remnant lesion, a lymphatic drainage area, or a primary lesion that is exposed by tumor resection during surgery. The IORT may replace the conventional external radiotherapy and be used widely in joint treatments of tumors in head and neck, chest, abdomen, and pelvic. The early IORT uses a conventional accelerator, and it requires to move the patient whose body is cut open in the surgery from the operation room to the accelerator machine room for operative radiotherapy, which movement greatly increases the risk of the operation, and the ambient conditions in the machine room also increases the risk of the operation. Thus, popularization of the IORT is extremely limited.

In the late 1990s, Hitesys S.P.A. in Italy firstly launched a mobile IORT apparatus NOVAC7, details of which are described in a U.S. Pat. No. 5,635,721 entitled "AN APPARATUS FOR THE ACCELERATION OF ELECTRONS, PARTICULARLY FOR INTRAOPERATIVE RADIOTHERAPY". The apparatus uses an electron linear accelerator that is small in size and light in weight, and it can be moved directly into the operation room for the IORT treatment. A radiation head of the electron linear accelerator is supported by a mechanical arm and has six degrees of freedom in space. With an automatic control technique, the radiation head can be moved by the mechanical arm into a surgical field, aim at a tumor bed, and perform intraoperative radiotherapy.

Afterwards, Intraop Medical Inc. in the United States launched another mobile electron linear accelerator MOBETRON dedicated for an IORT apparatus, which is detailed in a U.S. Pat. No. 5,321,271 entitled "INTRAOPERATIVE ELECTRON BEAM THERAPY SYSTEM AND FACILITY". The mobile electron linear accelerator includes a C-shaped arm to support and move a radiation head of the linear accelerator, and the radiation head may be moved in an automatic control manner into an operative field, aim at a tumor bed and perform electron beam irradiation.

A Chinese patent No. ZL200310108091.2 entitled "APPARATUS FOR INTRAOPERATIVE RADIOTHERAPY" discloses a new apparatus for intraoperative radiotherapy. The apparatus uses a CT and MRI 3D-image reconstruction software to reconstruct a 3D image of a lesion area of a tumor patient, and uses a simulation technique that simulates radiation incident onto a lesion to determine direction, angle and position of an electron beam incident onto the lesion. The radiation head of the electron linear accelerator is fixed to the ceiling of the operation room through a motion frame, and it may be placed at a predetermined position for intraoperative radiotherapy by moving the motion frame and an operation couch.

All of the above radiotherapy apparatuses are featured by the electron linear accelerator with a special design having reduced weight and size, and the radiation head of the accelerator can be oriented in any direction to radiate by using a multi-degree-of-freedom mechanical motion frame, which relates to robot technologies, multi-degree-of-freedom motion automatic control technologies, and manufacture technologies for manufacturing electron linear accelerators with light weight and small size. They represent the cutting-edge technical level at present.

Nevertheless, the above apparatuses still have following defects. Firstly, there is no three-dimensional stereotaxic apparatus or technology for clinical applications, and it relies only on eye observation of clinical surgeons and radiologists, or with assistance of CT or MRI image before operation, to determine position of the tumor bed. It is impossible to precisely determine position, angle, direction, and relationship with respect to surrounding normal tissues and organs at risk of the lesion in a state where the tumor bed is exposed, and thus it is impossible to determine an optimum incident path and direction, emission power, and irradiation time of the electron beam. Secondly, in clinical treatment, a radiologist needs to firstly place an applicator on a position to be irradiated of the patient by hand, and then fix the applicator onto the operation couch through a fixture device, and then observe the laser-positioning marker while remotely controlling the radiation head of the accelerator to move so as to ensure that the central axis of the radiation beam is aligned to the central axis of the applicator, and finally carry out the treatment. The above steps are complex and tedious, heavy in workload, and time-consuming, and they increase the risk of intraoperative radiotherapy. In addition, the positioning precision of the radiation head cannot be ensured, and it is difficult to implement precise intraoperative radiotherapy.

SUMMARY

An aspect of the present invention is to provide an apparatus for intraoperative radiotherapy with multiple robotic arms that utilizes ultrasound or other imaging technologies to provide guidance for the intraoperative radiotherapy so as to avoid injury of the electron beam to normal tissues and organs at risk of the patient, which can determine location of the lesion and radiation dose and time more precisely and thus reduce or avoid IORT complications and toxic side effects caused by radiation. By cooperative operation of multiple robotic arms with automatic control technologies, workload of clinical surgeons and radiologists can be greatly reduced, and positioning precision of the radiation head of the linear accelerator and the applicator can be improved, which are beneficial to achieve more precise intraoperative radiotherapy.

According to an exemplary embodiment of the present invention, a multi-robotic arm apparatus for intraoperative radiotherapy may comprise a chassis, a main robotic arm mounted on the chassis for moving a radiation head installed at an end thereof, a first robotic arm mounted on the chassis having a first robotic arm end gripper for gripping an imaging device or a treatment applicator, and a second robotic arm mounted on the chassis having a second robotic arm end gripper for gripping a simulation applicator.

In some embodiments, the first robotic arm and the second robotic arm are positioned at both sides of the main robotic arm, respectively.

In some embodiments, the chassis comprises a chassis body, and a first support leg and a second support leg fixedly connected to both sides of the chassis body having a two-dimensional motion platform installed thereon, a beam stopper being installed on the two-dimensional motion platform.

In some embodiments, four or more castors are mounted under the chassis body, the first support leg, and the second support leg to facilitate movement of the multi-robotic arm apparatus for intraoperative radiotherapy.

In some embodiments, the main robotic arm, the first robotic arm and the second robotic arm each have a multi-degree-of-freedom serial robotic arm architecture.

In some embodiments, the main robotic arm, the first robotic arm and the second robotic arm each have a six-degree-of-freedom serial robotic arm architecture.

In some embodiments, the second robotic arm is configured to grip the simulation applicator through the second robotic arm end gripper and move the simulation applicator to align it to a to-be-irradiated area in an operative field.

In some embodiments, the first robotic arm is configured to grip the imaging device through the first robotic arm end gripper and move the imaging device into the simulation applicator to obtain an image of the to-be-irradiated area, and the image is used for radiation treatment planning.

In some embodiments, the first robotic arm is further configured to grip the treatment applicator through the first robotic arm end gripper and position the treatment applicator within the simulation applicator according to the radiotherapy plan.

In some embodiments, the main robotic arm is configured to move, according to the radiotherapy plan, the radiation head to attach to an upper end surface of the treatment applicator so as to perform the radiotherapy.

In some embodiments, the second robotic arm is configured to hold the simulation applicator in a fixed position from the imaging stage to the radiotherapy stage.

According to another exemplary embodiment of the present invention, a multi-robotic arm apparatus for intraoperative radiotherapy may comprise a chassis including a chassis body and left and right support legs fixedly connected to both sides of the chassis body, a base of a main robotic arm being fixedly connected to a top of the chassis body, a radiation head of a linear accelerator being fixedly connected to an end of the main robotic arm, a base of a left robotic arm being fixedly connected to a left side of the chassis body, a left robotic arm end gripper being fixedly connected to an end of the left robotic arm for gripping an ultrasonic probe or other imaging devices, a base of the right robotic arm being fixedly connected to a right side of the chassis body, and a right robotic arm end gripper being fixedly connected to an end of the right robotic arm for gripping a simulation applicator.

In some embodiments, two castors are installed under the bottom of the chassis body, and one castor is installed under each of the left and right support legs. The castors are ordinary castors or universal castors that are driven by a motor, and the multi-robotic arm apparatus for intraoperative radiotherapy may move (e.g., translate), by motor driving, to any desired position and stop there.

In some embodiments, the main robotic arm may employ a six-degree-of-freedom serial robotic arm architecture. Each joint of the main robotic arm may be driven by a motor and equipped a position sensor. The main robotic arm may move the radiation head of the linear accelerator to any desired position and angle.

In some embodiments, the left robotic arm may employ a six-degree-of-freedom serial robotic arm architecture. Each joint of the left robotic arm may be driven by a motor and equipped with a position sensor.

In some embodiments, the gripper of the left robotic arm may automatically replace the ultrasonic probe or other imaging devices with a treatment applicator (or it is replaced by a human hand), and the left robotic arm may move the imaging device or the treatment applicator to any desired position and angle.

In some embodiments, the right robotic arm may employ a six-degree-of-freedom serial robotic arm architecture. Each joint of the right robotic arm may be driven by a motor and equipped with a position sensor. The right robotic arm may operate in a power assist mode to assist the clinician to manually place the simulation applicator to any desired position and angle.

In some embodiments, the multi-robotic arm apparatus for intraoperative radiotherapy may further comprise a two-dimensional motion platform mounted on the two support legs of the chassis and a beam stopper mounted on the two-dimensional motion platform. The two-dimensional motion platform may move the beam stopper linearly in x and y directions.

In some embodiments, the beam stopper is a rectangular metal plate having a certain thickness.

In some embodiments, the multi-robotic arm apparatus for intraoperative radiotherapy may further comprise a treatment couch fixed in the operation room. The treatment couch may perform lifting and rotation motions.

The present invention has the following beneficial effects: before the intraoperative radiotherapy, the robotic arm may move the ultrasonic probe or other imaging devices to take a three-dimensional image of a tumor bed, based on which position of a tumor target and relation of the target with respect to surrounding normal tissues and organs at risk may be precisely determined and then a plan for the intraoperative radiotherapy may be established by using an intraoperative radiotherapy planning system, thereby irradiation angle, direction, position, dose and time of the electron beam radiation may be determined more scientifically and rationally; as all the three robotic arms are mounted on the same chassis, a uniform coordinate system may be established for them, and a position of the tumor obtained according to the image from the ultrasound device or other imaging devices may be associated to a position of the radiation head of the linear accelerator easily and accurately so that the main robotic arm may be directed to move the radiation head of the linear accelerator to align to the tumor target in multiple directions with high precision; placement of the simulation applicator and the treatment applicator may be accomplished with assistance of the robotic arm, which saves a lot of complicated manual operations, greatly reduces the burden on the clinicians, saves the treatment time, and reduces the risk of intraoperative radiotherapy.

DESCRIPTION OF EMBODIMENTS

Hereinafter the present invention will be described in more detail with reference to the drawings in order to make the technical solutions, creative features, achievements and effects of the present invention easy to understand.

Figure 1:
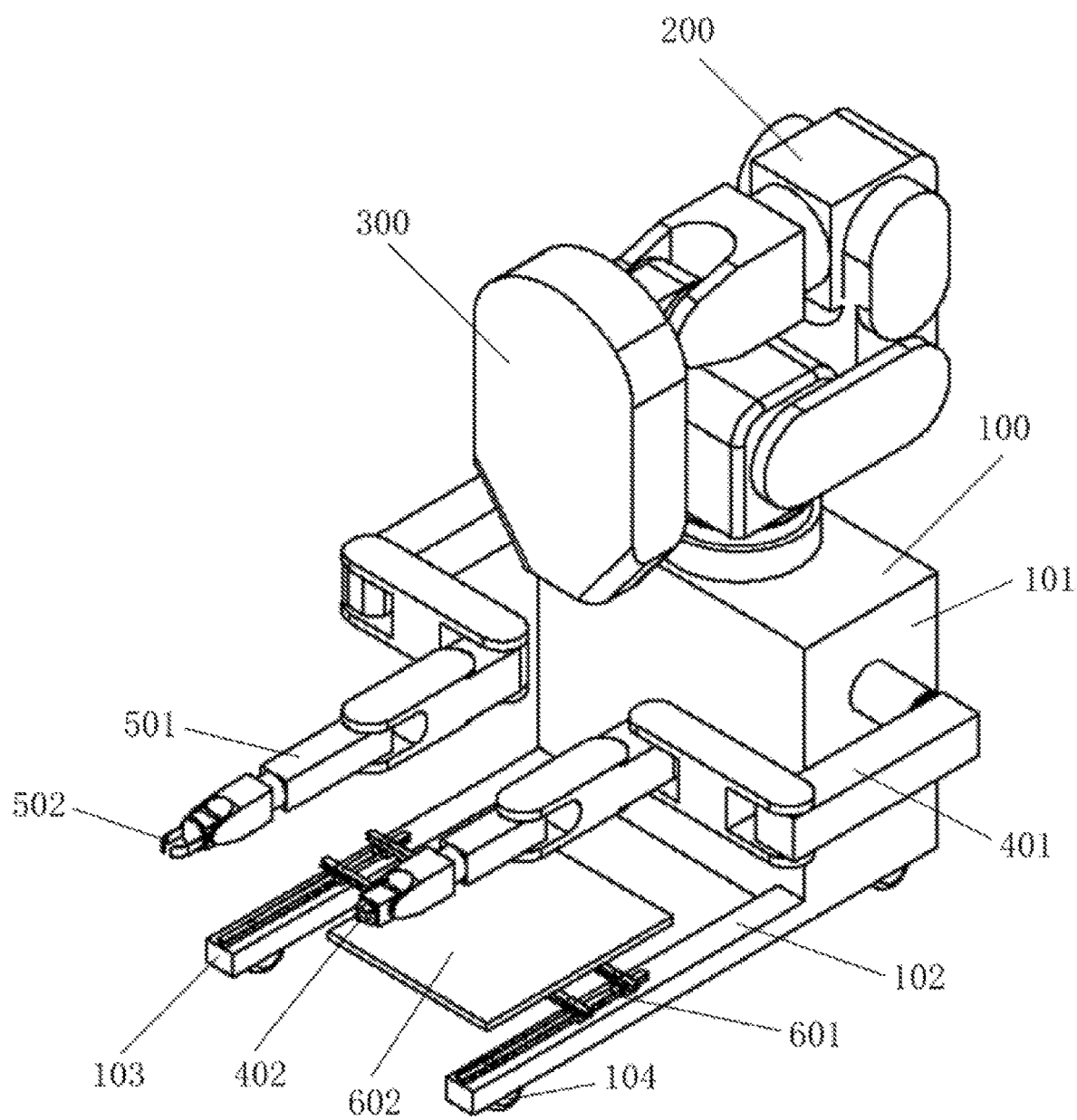
FIG. 1 is a schematic diagram showing a multi-robotic arm apparatus for intraoperative radiotherapy in an initial state according to an embodiment of the present invention.

FIG. 1 shows a multi-robotic arm apparatus for intraoperative radiotherapy according to an embodiment of the present invention. The multi-robotic arm apparatus for intraoperative radiotherapy is shown in an initial retraction state so as to facilitate movement of the multi-robotic arm apparatus.

As shown in FIG. 1, the multi-robotic arm apparatus for intraoperative radiotherapy according to an embodiment of the present invention may include a chassis 100, a main robotic arm 200, a linear accelerator radiation head 300, a left robotic arm 401, a left robotic arm end gripper 402, a right robotic arm 501, a right robotic arm end gripper 502, a two-dimensional motion platform 601, and a beam stopper 602.

The chassis 100 includes a chassis body 101, and left and right support legs 102, 103 fixedly connected to the chassis body 101 at two sides, respectively. Preferably, the chassis body 101 may be equipped with castors 104 under the bottom thereof, for example, two castors as shown in FIG. 1, and the left and right support legs each are also equipped with a castor. The castors may be ordinary castors or universal castors driven by a motor that may be remotely controlled by a doctor so as to move the multi-robotic arm apparatus for intraoperative radiotherapy to a designated treatment position in the operation room and fix it there.

A base of the main robotic arm 200 may be fixedly connected to the top of the chassis body 101. Preferably, the main robotic arm 200 may utilize but not limited to a six-degree-of-freedom serial robotic arm architecture. Each joint of the main robotic arm 200 may be driven by a motor, and at each joint is equipped with a position sensor for monitoring a rotation angle of each joint in real time.

The linear accelerator radiation head 300 may be fixedly connected to the end of the main robotic arm 200. With automatic control technologies, the main robotic arm 200 may move the linear accelerator radiation head 300 to any desired position and angle.

A base of the left robotic arm 401 may be fixedly connected to the left side of the chassis body 101. Preferably, the left robotic arm 401 may utilize but not limited to a six-degree-of-freedom serial robotic arm architecture. Each joint of the left robotic arm 401 may be driven by a motor, and at each joint is equipped with a position sensor for monitoring a rotation angle of the joint in real time. The left robotic arm end gripper 402 may be fixedly connected to the end of the left robotic arm 401. Preferably, the left robotic arm end gripper 402 may grip an ultrasonic probe 403 or other imaging devices, which may be replaced with a treatment applicator 404 automatically or by a human hand.

With automatic control technologies, the left robotic arm 401 may move the ultrasonic probe 403 or the treatment applicator 404 to any desired position and angle.

A base of the right robotic arm 501 may be fixedly connected to the right side of the chassis body 101. Preferably, the right robotic arm 501 may utilize but not limited to a six-degree-of-freedom serial robotic arm architecture. Each joint of the right robotic arm 501 may be driven by a motor, and at each joint is equipped with a position sensor for monitoring a rotation angle of the joint in real time. The right robotic arm end gripper 502 may be fixedly connected to the end of the right robotic arm 501 for gripping the simulation applicator 503. Preferably, the right robotic arm 501 may operate in a power assist mode to assist the clinicians to manually place the simulation applicator 503 to any desired position and angle.

Although in the above description each of the main robotic arm 200, the left robotic arm 401 and the right robotic arm 501 has the six-degree-of-freedom serial robotic arm architecture, it should be understood that the present invention is not limited thereto. Instead, with a proper location, each robotic arm may have multiple degrees of freedom such as two degrees of freedom, three degrees of freedom, four degrees of freedom and the like, preferably three or more degrees of freedom, more preferably four or more degrees of freedom, for example, six degrees of freedom, as long as relevant components may be manipulated conveniently to achieve different positions, orientations or the like. Structure and precise control of the robotic arms are well known in the art, and details thereof will not be set forth herein.

The two-dimensional motion platform 601 may be mounted on the two support legs of the chassis 100. The beam stopper 602 may be a rectangular metal plate having a certain thickness and it may be mounted on the two-dimensional motion platform 601. The two-dimensional motion platform 601 may move the beam stopper 602 linearly in x and y directions so that a central axis of an electron beam emitted from the linear accelerator radiation head 300 may be incident at or near a central position of the beam stopper 602.

As shown in FIG. 1, each robotic arm of the multi-robotic arm apparatus for intraoperative radiotherapy may be in an initial retraction state so as to facilitate movement of the apparatus. The four castors 104 under the bottom of the chassis 100 may be driven by a motor, which may be remotely controlled by a clinician so as to move the intraoperative radiotherapy apparatus to a designated treatment position in the operation room and fix it there.

Figure 2:
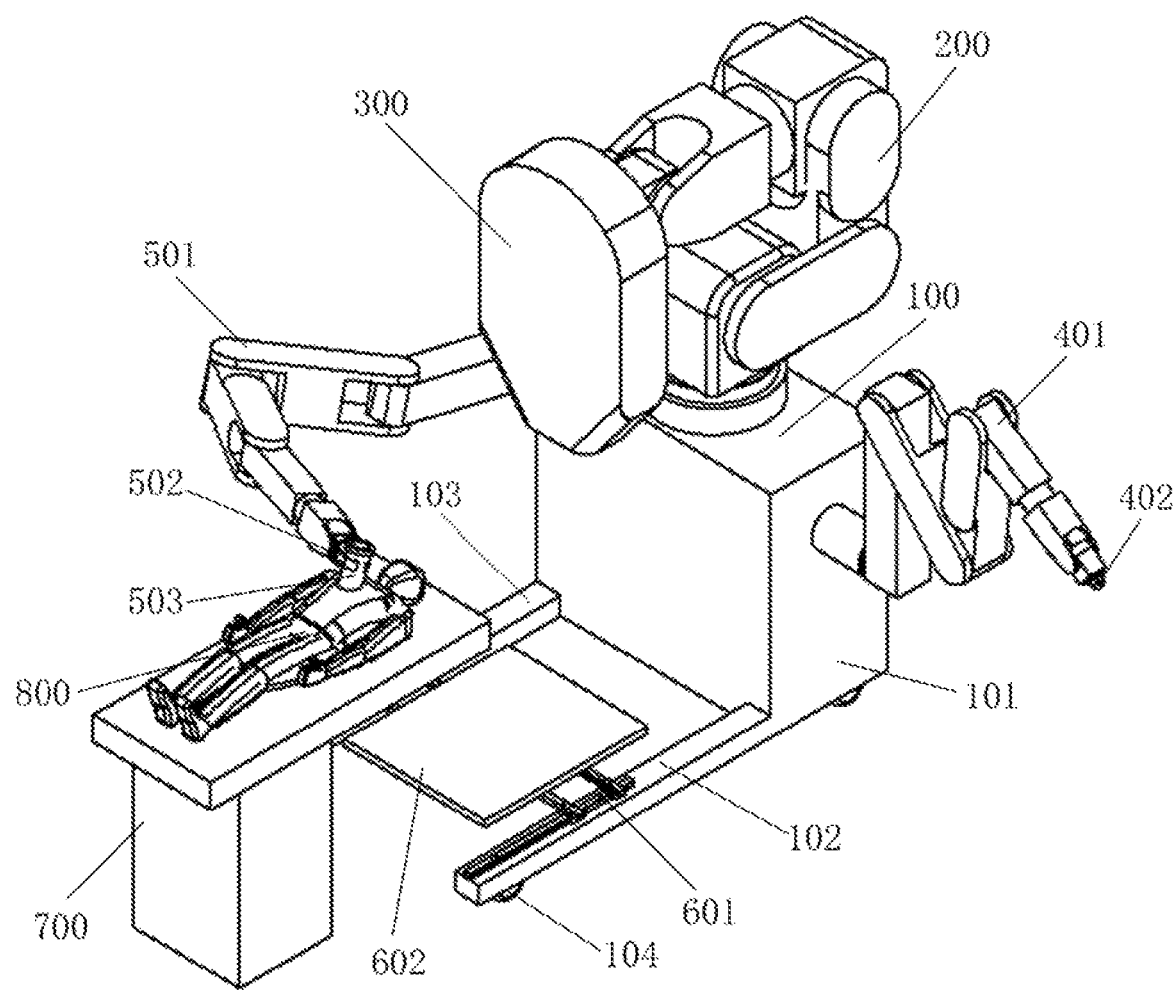
FIG. 2 is a schematic diagram showing a multi-robotic arm apparatus for intraoperative radiotherapy in a positioning state according to an embodiment of the present invention.

FIG. 2 shows a multi-robotic arm apparatus for intraoperative radiotherapy in a positioning simulation state according to an embodiment of the present invention. As shown in FIG. 2, the right robotic arm end gripper 502 may grip the simulation applicator 503, and the treatment couch 700 is fixed in the operation room. Preferably, the treatment couch 700 may perform lifting and rotating motions.

In an example, a human body 800 may be secured on the treatment couch 700. By moving of the multi-robotic arm intraoperative radiotherapy apparatus and rotating or lifting of the treatment couch 700, the human body 800 may be in a position that is convenient for radiotherapy. Preferably, the right robotic arm end gripper 502 grips the simulation applicator 503, and each moving joint of the right robotic arm 501 is equipped with a power assist motor and a joint position sensor. The clinician may manually manipulate the right robotic arm 501 so as to move the simulation applicator 503 to align to a to-be-irradiated area of the human body 800 in the operation field. Position of the end of the simulation applicator 503 may be precisely determined by the joint position sensors of the right robotic arm 501.

Figure 3:
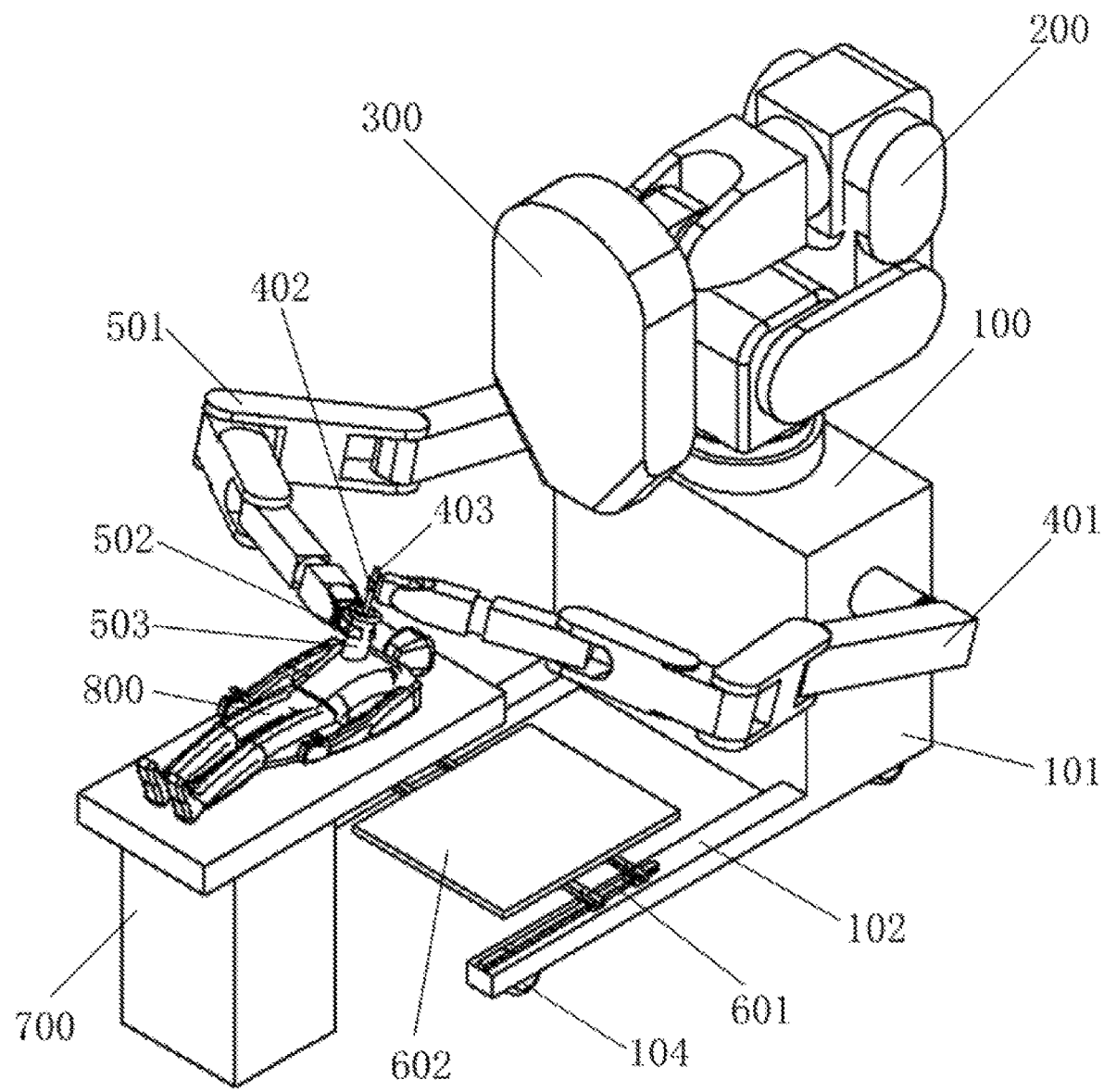
FIG. 3 is a schematic diagram showing a multi-robotic arm apparatus for intraoperative radiotherapy in an imaging state according to an embodiment of the present invention.

FIG. 3 shows a multi-robotic arm intraoperative radiotherapy apparatus in an imaging state according to an embodiment of the present invention.

In an example, the left robotic arm end gripper 402 may grip an ultrasonic detector 403 or other imaging devices. Each joint of the left robotic arm 401 may be driven by a motor, and an automatic control system may drive the left robotic arm 401 to move the ultrasonic probe 403 or other imaging devices into the simulation applicator 503 according to position parameters of the end of the simulation applicator 503. At each moving joint of the left robotic arm 401 is equipped with a position sensor by which the position of the ultrasonic probe 403 or other imaging devices may be determined in real time using a spatial position resolution algorithm, and thus positions of the tumor, normal tissues and organs at risk in the image may be determined. Then, the radiologist may design an intraoperative radiotherapy plan using a radiotherapy planning system and the obtained images and determine electron beam radiation angle, direction, position, and irradiation dose and time.

Preferably, after obtaining the image of the target area, the left robotic arm 401 may automatically move the ultrasonic probe 403 or other imaging devices out of the simulation applicator 503, and the ultrasonic probe 403 or other imaging devices may be replaced with a treatment applicator 404 automatically or by a human hand so as to facilitate subsequent radiotherapy. Preferably, the left robotic arm end gripper 402 may grip not only the ultrasonic probe 403 or other imaging devices, but also the treatment applicator 404.

Figure 4:
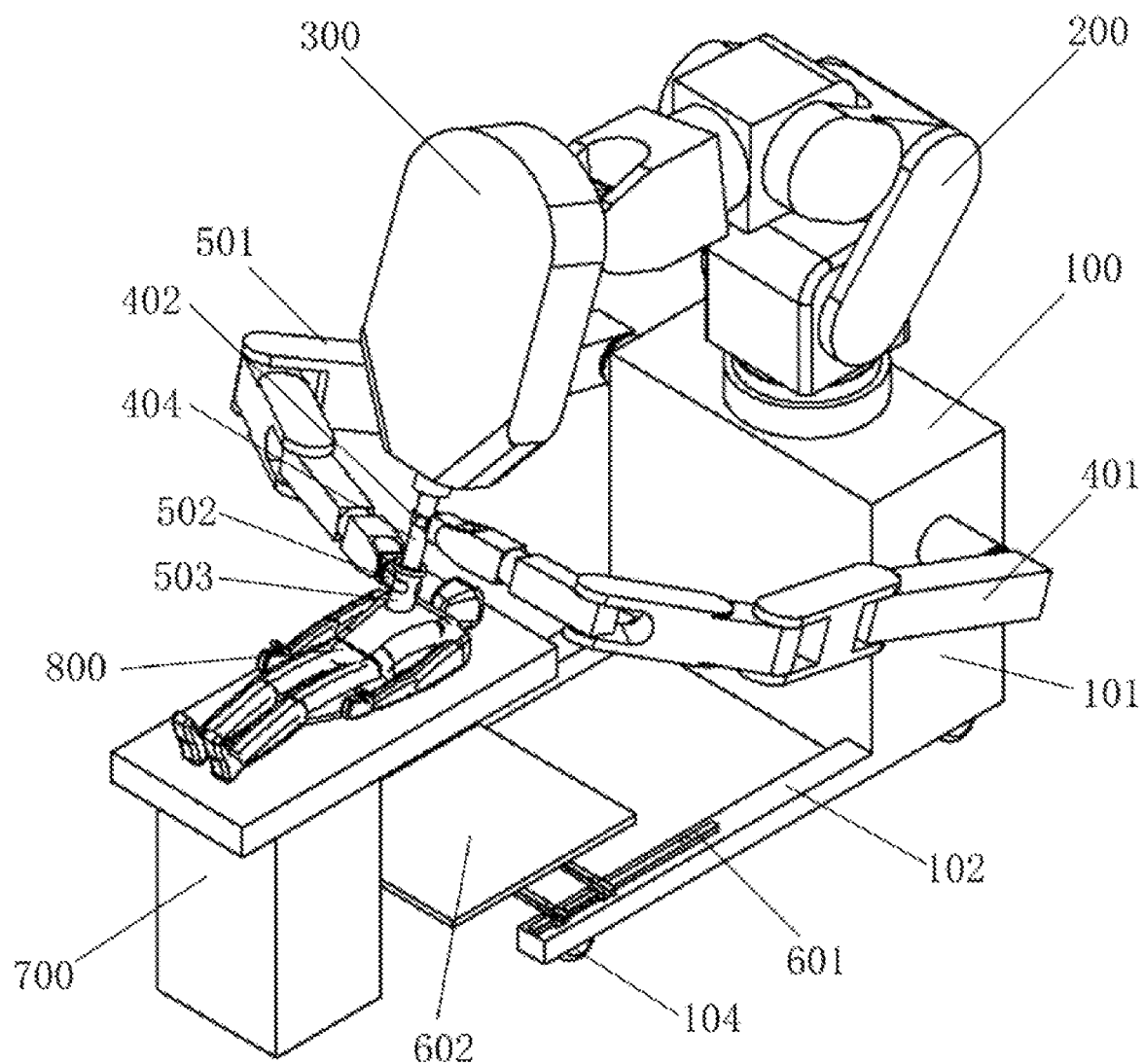
FIG. 4 is a schematic diagram showing a multi-robotic arm apparatus for intraoperative radiotherapy in a treatment state according to an embodiment of the present invention.

FIG. 4 shows a multi-robotic arm intraoperative radiotherapy apparatus in a treatment state according to an embodiment of the present invention.

As shown in FIG. 4, the left robotic arm end gripper 402 may grip the ultrasonic probe 403 or other imaging devices, which may be replaced with the treatment applicator 404 automatically or by human hand. With automatic control technologies, the left robotic arm 401 may move the ultrasonic probe 403 or the treatment applicator 404 to any desired position and angle.

In an example, after obtaining the image of the target area, the left robotic arm end gripper 402 may automatically move the ultrasonic probe 403 or other imaging devices out of the simulation applicator 503, and the ultrasonic probe 403 or other imaging devices may be replaced with the treatment applicator 404 automatically or by a human hand so as to facilitate subsequent radiotherapy.

In an example, the left robotic arm end gripper 402 may grip the treatment applicator 404. The left robotic arm end gripper 402 may automatically place the treatment applicator 404 into the simulation applicator 503. The placement angle, direction, and position of the treatment applicator 404 may be determined by the intraoperative radiotherapy planning system. Preferably, the main robotic arm 201 may automatically move the linear accelerator radiation head 300 to attach to the upper end surface of the treatment applicator 404 according to the irradiation angle, direction determined by the radiotherapy planning system. Preferably, the two-dimensional motion platform 601 may automatically move in a two-dimensional plane to move the beam stopper 602 to a certain position such that the center of the electron beam is incident at or near the geometric center of the beam stopper 602 which attenuates or blocks the radiation passing through the human body and the treatment couch.

From the imaging stage to the radiotherapy stage as described above, the right robotic arm 501 may hold the simulation applicator 503 in the fixed position, and the multi-robotic arm system may establish a coordinate system based on the position of the simulation applicator 503. That is to say, all operations from the imaging stage to the radiotherapy stage may be performed in the same coordinate system. It may improve consistency of the various operations, and thus improve precision of the intraoperative radiotherapy.

Preferably, after the intraoperative radiotherapy, the main robotic arm 201 may automatically return the linear accelerator radiation head 300 to the standby position as shown in FIG. 1, and the left robotic arm end gripper 402 may automatically remove the treatment applicator 404 from the simulation applicator 503 and return to the standby position as shown in FIG. 2. At last, with the power assistance of the right robotic arm 501, the clinician may manually move the simulation applicator 503 from the operation filed of the human body 800 to the standby position, thereby completing the intraoperative radiotherapy.

The principles of the present invention have been described above with reference to specific embodiments. It will be understood by those skilled in the art that the present invention is not limited to the above embodiments, and many modifications and variations may be made in form and detail without departing from the spirit and scope of the present invention. The scope of the present invention is defined by the accompanying claims and their equivalents.

What is claimed and desired to be secured by Letters Patent of the United States is:

1. A multi-robotic arm apparatus for intraoperative radiotherapy comprising:
   a chassis;
   a main robotic arm mounted on the chassis for moving a radiation head installed at an end of the main robotic arm;
   a first robotic arm mounted on the chassis having a first robotic arm end gripper for gripping an imaging device or a treatment applicator; and
   a second robotic arm mounted on the chassis having a second robotic arm end gripper for gripping a positioning applicator,
   wherein the positioning applicator is positioned to align to a to-be-irradiated area in an operative field in a positioning simulation stage so as to determine a position of the positioning applicator, and the treatment applicator is placed into the positioning applicator in a radiotherapy stage.

2. The multi-robotic arm apparatus for intraoperative radiotherapy of claim 1 wherein the first robotic arm and the second robotic arm are positioned at opposite sides of the main robotic arm, respectively.

3. The multi-robotic arm apparatus for intraoperative radiotherapy of claim 1 wherein the chassis comprises:
   a chassis body; and
   a first support leg and a second support leg fixedly connected to opposite sides of the chassis body, respectively.

4. The multi-robotic arm apparatus for intraoperative radiotherapy of claim 3 further comprising a two-dimensional motion platform mounted on the first and second support legs.

5. The multi-robotic arm apparatus for intraoperative radiotherapy of claim 4 further comprising a beam stopper mounted on the two-dimensional motion platform.

6. The multi-robotic arm apparatus for intraoperative radiotherapy of claim 3 wherein under the chassis body, the first support leg and the second support leg are mounted four or more castors to facilitate movement of the multi-robotic arm apparatus for intraoperative radiotherapy.

7. The multi-robotic arm apparatus for intraoperative radiotherapy of claim 1 wherein the main robotic arm, the first robotic arm and the second robotic arm each have a multi-degree-of-freedom serial robotic arm architecture.

8. The multi-robotic arm apparatus for intraoperative radiotherapy of claim 7 wherein the main robotic arm, the first robotic arm and the second robotic arm each have a six-degree-of-freedom serial robotic arm architecture.

9. The multi-robotic arm apparatus for intraoperative radiotherapy of claim 1 wherein the second robotic arm is configured to operate in a power assist mode to assist a clinician to manually place the positioning applicator to a desired position and angle.

10. The multi-robotic arm apparatus for intraoperative radiotherapy of claim 1 wherein the first robotic arm is configured to grip the imaging device through the first robotic arm end gripper and move the imaging device into the positioning applicator to obtain an image of the to-be-irradiated area in an imaging stage, and the image of the to-be-irradiated area is used to make a plan for the intraoperative radiotherapy.

11. The multi-robotic arm apparatus for intraoperative radiotherapy of claim 10 wherein the first robotic arm is configured to grip the treatment applicator through the first robotic arm end gripper and position the treatment applicator within the positioning applicator according to the intraoperative radiotherapy plan in the radiotherapy stage.

12. The multi-robotic arm apparatus for intraoperative radiotherapy of claim 11 wherein the main robotic arm is configured to move, according to the intraoperative radiotherapy plan, the radiation head to attach to an upper end surface of the treatment applicator so as to perform the intraoperative radiotherapy.

13. The multi-robotic arm apparatus for intraoperative radiotherapy of claim 12 wherein the second robotic arm is configured to hold the positioning applicator in a fixed position from the imaging stage to the radiotherapy stage.

14. The multi-robotic arm apparatus for intraoperative radiotherapy of claim 13 wherein from the imaging stage to the radiotherapy stage, the main robotic arm, the first robotic arm and the second robotic arm operate in a same coordinate system established based on the fixed position of the positioning applicator.

* * * * *